United States Patent
Khan

(10) Patent No.: US 8,883,494 B2
(45) Date of Patent: Nov. 11, 2014

(54) IN VITRO MODEL FOR NEURONAL DEATH

(76) Inventor: Adil A. Khan, Baltimore, MD (US)

( * ) Notice: Subject to any disclaimer, the term of this patent is extended or adjusted under 35 U.S.C. 154(b) by 482 days.

(21) Appl. No.: 12/013,921

(22) Filed: Jan. 14, 2008

(65) Prior Publication Data

US 2008/0227201 A1    Sep. 18, 2008

Related U.S. Application Data

(62) Division of application No. 10/989,918, filed on Nov. 15, 2004, now abandoned.

(60) Provisional application No. 60/520,285, filed on Nov. 14, 2003.

(51) Int. Cl.
| | |
|---|---|
| C12N 5/00 | (2006.01) |
| C12N 5/074 | (2010.01) |
| C12N 5/0735 | (2010.01) |
| C12N 5/0793 | (2010.01) |
| G01N 33/50 | (2006.01) |

(52) U.S. Cl.
CPC .......... *C12N 5/0619* (2013.01); *G01N 33/5058* (2013.01); *C12N 2500/36* (2013.01); *C12N 2503/02* (2013.01)
USPC ........................................................ 435/325

(58) Field of Classification Search
None
See application file for complete search history.

(56) References Cited

U.S. PATENT DOCUMENTS

| | | | | |
|---|---|---|---|---|
| 2003/0152558 | A1* | 8/2003 | Luft et al. ................... | 424/93.21 |
| 2003/0224345 | A1* | 12/2003 | West et al. ..................... | 435/4 |

OTHER PUBLICATIONS

Kilsdonk et al., JBC 270: 17250-17256, 1995.*
Thomson et al. PNAS 92: 7844-7848, 1995.*
Simons and Toomre (Nature Rev 1: 31-41, 2000).*
Bromley, S. K. et al. The immunological synapse. Annu. Rev. Immunol. 2001;19:375-396.
Khan A. A. et al., Physiological regulation of the immunological synapse by agrin. Science. 2001;292(5522):1681-6.
Simons, K. & Ikonen E. Functional rafts in cell membranes. Nature. 1997;387:569-572.
Villalba M. et al., Vav1/Rac-dependent actin cytoskeleton reorganization is required for lipid raft clustering in T cells. J. Cell Biol. 2001;155:331-338.
Zacco A. et al., 3-Hydroxy-3-Methylglutaryl Coenzyme A Reductase Inhibitors Protect Cortical Neurons from Excitotoxicity. J. Neurosci. 2003;23:11104-11111.
Lee O. K. et al., Fluvastatin and lovastatin but not pravastatin induce neuroglial differentiation in human mesenchymal stem cells. J. Cell Biochem. 2004;93:917-28.
Dimmeler S. et al., HMG-CoA reductase inhibitors (statins) increase endothelial progenitor cells via the PI 3-kinase/Akt pathway. J. Clin. Invest. 2001;108:391-7.
Kusuyama T. et al., The effects of HMG-CoA reductase inhibitor on vascular progenitor cells. J. Pharmacol. Sci. 2006;101:344-9.
Khan, A.A. et al., Neuroglobin attenuates β-amyloid neurotoxicity in vitro and transgenic Alzheimer phenotype in vivo. Proc. Natl. Acad. Sci. U.S.A. 2007;104(48):19114-19119.
Schneider, A. et al., Flotillin-dependent clustering of the amyloid precursor protein regulates its endocytosis and amyloidogenic processing in neurons. J. Neurosci. 2008;28(11):2874-2882.
Khan, A.A. et al., Regulation of hypoxic neuronal death signaling by neuroglobin. FASEB J. Jan. 15, 2008, [Epub ahead of print].
Alfsen, A. et al. HIV-1-infected blood mononuclear cells form an integrin- and agrin-dependent viral synapse to induce efficient HIV-1 transcytosis across epithelial cell monolayer. Mol. Biol. Cell. 2005;16, 4267-4279.
Jolly, C. & Sattentau, Q.J. Human immunodeficiency virus type 1 virological synapse formation in T cells requires lipid raft integrity. J. Virol. 2005;79(18):12088-12094.
Kirchstein, R. & Skirboll, L.R. Stem Cells: Scientific progress and future research directions, Chapter 4 ("The adult stem cell"), pp. 23-42, Department of Health and Human Services. Jun. 2001. <http://stemcells.nih.gov/info/scireport/2001report>.
Phillips, B.W. et al., Compactin enhances osteogenesis in murine embryonic stem cells. Biochem. Biophys. Res. Commun. 2001;284:478-484.

* cited by examiner

*Primary Examiner* — Daniel E Kolker
*Assistant Examiner* — Aditi Dutt
(74) *Attorney, Agent, or Firm* — Miles and Stockbridge

(57) ABSTRACT

This invention demonstrates the formation of a novel polarized membrane lipid raft signaling module in neurons, in response to several diverse neurotoxic stimuli. This polarization occurs well before neurons commit to die, and is an early mechanism in death signaling. The formation of this signaling module is dependent on cholesterol for its formation and provides a mechanistic explanation for the protective effects of cholesterol depleting drugs in several non-neural models of cell death. As such, the formation of the signaling module lends itself as a novel screen for the identification of new drugs and therapeutics which would retard its formation and protect against neuronal injury and death.

13 Claims, 5 Drawing Sheets

IN VITRO MODEL FOR NEURONAL DEATH

CROSS-REFERENCE TO RELATED APPLICATIONS

This Divisional U.S. patent application, filed under 37 C.F.R. §1.53(b) and 35 U.S.C. §121, claims the benefit of priority under 35 U.S.C. §120 of U.S. patent application Ser. No. 10/989,918, filed on 15 Nov. 2004, which claims the benefit under 35 U.S.C. §119(e)(1) of U.S. Provisional Patent Application No. 60/520,285, filed under 35 U.S.C. §111(b) on 14 Nov. 2003, each of which are hereby incorporated by reference in their entireties.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON COMPACT DISC

Not applicable.

BACKGROUND OF THE INVENTION

1. Field of the Invention

The field of the invention is neuronal death such as that which occurs during neurodegenerative diseases, and following stroke or trauma. The invention identifies a novel biochemical mechanism required to induce death in neurons from a variety of neurotoxic insults.

2. Description of the Related Art

Neuronal death underlies symptoms of neurodegenerative diseases (ND) and damage from stroke and trauma. Neuronal death in neurodegenerative diseases such as Alzheimer's Disease (AD) and Parkinson's Disease (PD) is characterized by a number of features, including: (a) memory loss; (b) language deterioration; (c) impaired motor skills; (d) poor judgment; and (e) indifferent attitude. Although AD usually begins after age 60, its onset may occur as early as age 40. AD first appears as memory decline. As the disease progresses over several years, cognition, personality, and the ability to function are all impaired or destroyed.

There is no cure for AD and no way to slow the progression of the disease. For some people in the early or middle stages of the disease, medication such as tacrine may alleviate some cognitive symptoms. Also, some medications may help control behavioral symptoms such as sleeplessness, agitation, wandering, anxiety. and depression. These treatments are aimed solely at making the patient more comfortable and do nothing to slow the progression of the underlying neuronal death in the disease.

As such, there is much ongoing research that is aimed at the identification and development of new therapeutic agents which can at least slow, if not reverse, the death of neurons in AD and other neurodegenerative diseases or following stroke or trauma.

An important tool in the identification of therapeutic agents for neuronal death would be the development of an in vitro model of neuronal death, which would replicate the biochemical steps involved in the death process. Such an in vitro model would be invaluable for screening and developing potential therapeutic agents.

As such, there is intense interest in the development of a practical in vitro model for neuronal death, one which would exhibit biochemical features common to diverse stimuli.

In view of the intense interest in the development of practical neurodegenerative disease models, a number of mouse models for AD and PD have been developed to date. Despite the number of different mouse models that have been developed, no one animal model demonstrates the marked neuronal death accepted as being completely correlative of the degenerative disease condition. Thus, the biochemical mechanisms which underlie human ND disease and stroke related neuronal death are poorly understood.

Therefore, there is great interest in the elucidation of the signal transduction pathway which underlies neuronal death. This invention identifies a biochemical pathway used by all neurons in response to diverse neurotoxic stimuli. As such, it enables in vitro neuronal models which demonstrate reliable, reproducible neuronal death to be used as screens for compounds which would inhibit steps in the novel biochemical pathway. Such a model would greatly facilitate the identifications of compounds which could be used to alleviate human neuronal disease.

Cells throughout the body are dependent upon the ability of membrane receptors to bind ligands and to effectively signal a cascade of biochemical events from the membrane to the nucleus. In the immune system, ligand binding to receptor (i.e. antigen to antigen receptor) induces changes in the morphology of the cell through cytoskeletal reorganization and induces the nucleus to activate the transcription of new genes to promote cellular differentiation and/or proliferation. This change in cell morphology is known as capping and refers to a polarization process in which cell surface proteins migrate to a specific pole of the cell (Taylor et al., 1971). The molecular mechanism of capping is poorly understood. It is clear, however, that disruption of the polarization process disrupts immune signaling (Bourguignon and Bourguignon, 1984).

The plasma membrane of lymphoctes has recently been shown to contain discrete lipid microdomains referred to as "lipid rafts" (Parton and Simons, 1995; Bromley et al., 2001). The terminology lipid rafts indicates microdomains of the plasma membrane which were first identified based on their insolubility in certain nonionic detergents and are enriched in glycosphingolipids and cholesterol. This work has shown that the plasma membrane is not a uniform lipid bilayer but rather that it contains specialized lipid microdomains which act as signaling platforms for the transduction of external signals into cellular responses. The aggregation of lipid rafts is essential for signaling in cells throughout the body. Disruption of lipid raft aggregation through the use of inhibitors of lipid raft assembly (i.e. cholesterol depleters) abrogates cell signaling. The relationship between capping and lipid raft aggregation has been unclear but recent evidence demonstrates that signal transduction involves the selective movement of key signaling proteins into and out of lipid rafts organizing a signaling module. In the immune sytem, this signaling module has been termed the immunological synapse to describe the site of cell-cell contact between communicating immune cells. Such spatial contact and communication (i.e. cell-cell co-capping) is essential for all immune functions. Khan et al., 2001 provided evidence for the polypeptide agrin as the first endogenous mediator of immune polarization and lipid raft aggregation. This was the first description of an endogenous lipid raft assembly inducing protein. The applicant reasoned that the polarization of raft microdomains may be a conserved mechanism of biological signaling used by neurons for signal transduction. This invention describes the polarization of raft microdomains on the cell body/soma of neurons in response to external stimuli. It demonstrates that polarization of raft microdomains is a signal transduction mechanism utilized by a variety of neurotoxic stimuli during death signaling.

SUMMARY OF THE INVENTION

The cause and the mechanism by which neurons die in neurodegenerative diseases are unknown. The mechanism by which neurons die following stroke and trauma is also unknown.

Many damaged and dead neurons in autopsy brain sections from ND patients show condensed and fragmented chromatin, suggestive of apoptosis (a programmed cell death pathway). Further, treatment of cultured neurons in vitro induces chromatin condensation and fragmentation also suggestive of apoptosis.

Brain ischemia leads to two forms of neuronal death. Necrotic neuronal death occurs in regions of severe blood flow insufficiency, while in the surrounding regions (penumbra) where oxygen levels are higher and blood flow is less compromised, apoptotic neuronal death is observed. Apoptotic death is indicated by condensed and fragmented chromatin, suggesting an orderly yet unknown death mechanism.

Neurodegenerative diseases such as Alzheimer's Disease (AD) and Parkinson's Disease (PD) are characterized by marked neuronal death. Neuronal death also occurs following stroke and trauma, accounting for post-injury symptoms such as paralysis and cognitive loss. The signal transduction pathways involved in neuronal death in these situations are not well understood. In non-neural cells such as lymphocytes, reorganization of membrane microdomains (lipid rafts) mediates formation of signaling complexes involved in transducing proliferative and death signals. The applicant examined the surface distribution of raft membrane microdomains in in vitro cultures of cortical neurons after a variety of death stimuli, by using the raft marker cholera toxin B (CTx-B) subunit, which binds the glycosphingolipid $G_{M1}$. The applicant demonstrates that diverse insults such as beta-amyloid peptide (Aβ), reactive oxygen species (1 mM $H_2O_2$), NMDA, neurotrophic factor deprivation, axotomy, mitochondrial poisons (arsenite), fas ligand crosslinking and hypoxia induce rapid polarization of somal raft membranes. This polarization occurs well before neurons commit to die, consistent with a role as an early mechanism in death signaling.

The applicant's data demonstrate that many diverse neuronal insults induce the formation of a polarized lipid raft mitochondria signaling module. The applicant's results show the formation of this signaling module is causally related to neuronal death, as inhibition of its formation through a variety of drugs is protective against neurotoxic insult. As such, formation of the signaling module lends itself as a screen for the identification of new drugs and therapeutics, which would retard its generation and protect against neuronal injury and death.

An in vitro model for neuronal death, as well as methods for its preparation and use, is provided. The in vitro model is characterized by neurons undergoing a shared common biochemical pathway, i.e. the polarization of neuronal soma membrane lipid rafts, in response to a variety of death inducing stimuli. The in vitro model and mechanism finds use in a important application, namely the screening of potential therapeutic agents for neurodegenerative diseases and stroke and trauma.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 1 panel B shows the aggregation and polarization of raft microdomains to a pole of the neuronal cell body following 15 min. exposure to 25 µM A-beta 25-35 peptide. Similar raft microdomain polarization is seen following exposure to reactive oxygen species (1 mM $H_2O_2$), NMDA, neurotrophic factor deprivation, axotomy, mitochondrial poisons (e.g., arsenite), fas ligand crosslinking, and hypoxia. FIG. 1 panel C shows the inhibition of raft polarization following 15 min. exposure to 25 µM A-beta 25-35 peptide due to 1 hr pre-treatment with βCD, a cholesterol depleting agent.

DETAILED DESCRIPTION OF THE INVENTION

Figure 1A:
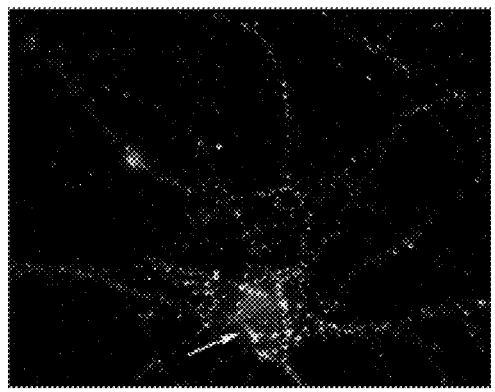
FIG. 1 panel A shows the distribution of lipid rafts in a resting cultured neuron. Raft distribution in clusters of cholera toxin B staining is uniformly distributed along the cell body surface.
Figure 1B:
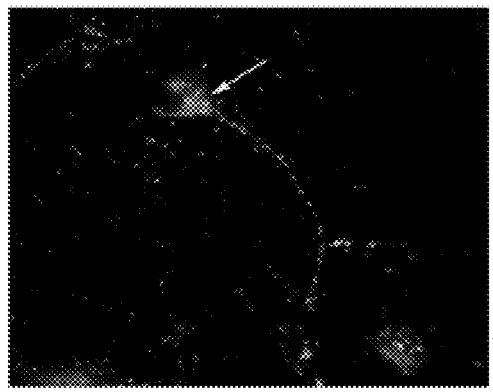
Figure 1C:
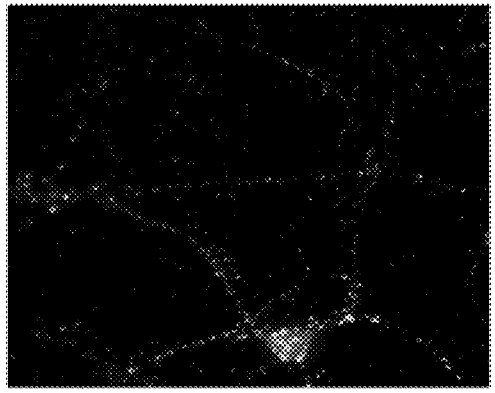
Figure 2A:
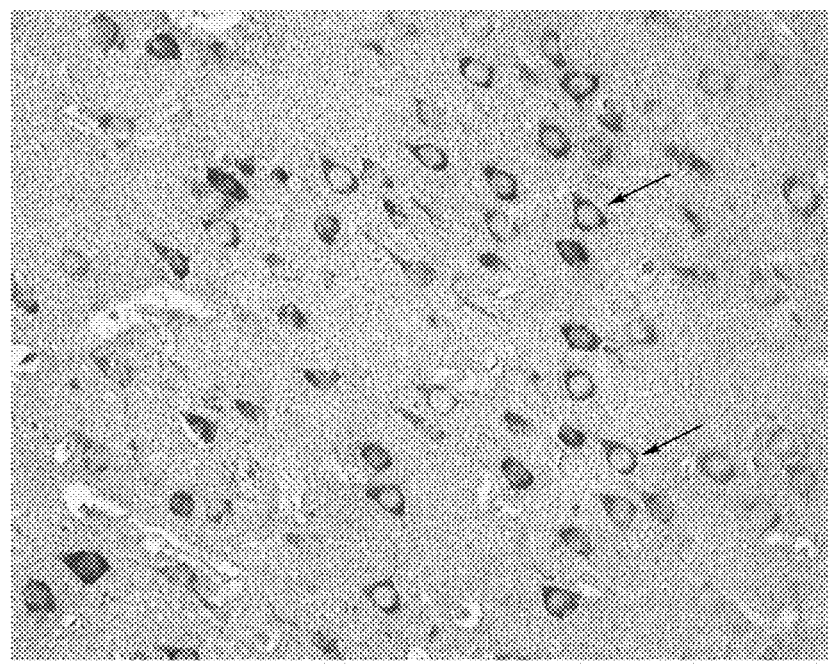
FIG. 2 shows staining for raft microdomains and A-beta peptide from brain tissue sections of normal (A) and Alzheimer's Disease individuals. Arrows in FIG. 2, panel A indicate uniform distribution of cholera toxin B staining around cell bodies of neurons in normal brain control. Arrows in FIG. 2, panel B indicate raft polarized microdomains co-stained and co-polarized with A-beta peptide.
Figure 2B:
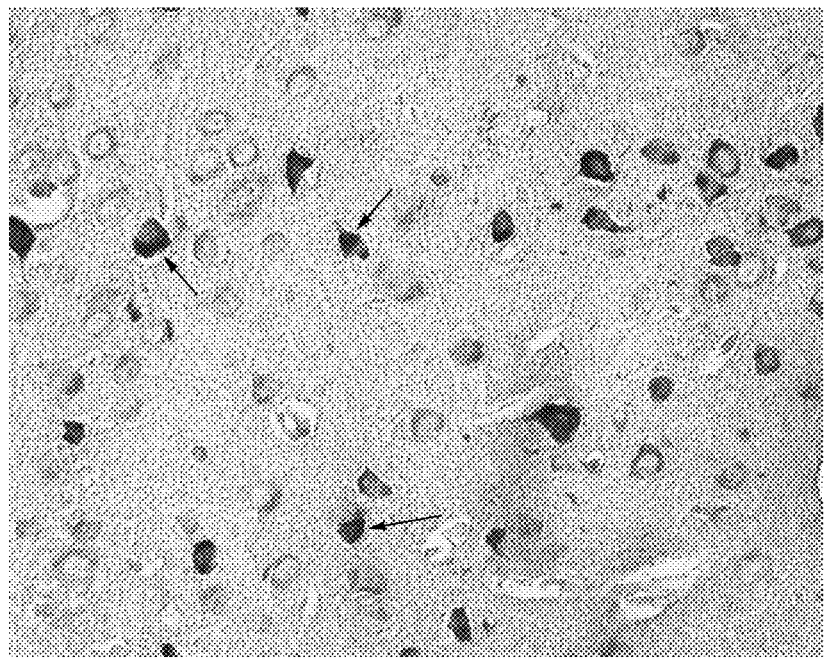

The signal transduction pathways involved in neuronal death are not well understood. In nonneural cells such as lymphocytes, reorganization of membrane microdomains (lipid rafts) mediates formation of signaling complexes involved in transducing proliferative and death signals. The surface distribution of raft membrane microdomains in cortical neuron cultures was examined after a variety of death stimuli, by using the raft marker cholera toxin B (CTx-B) subunit, which binds the glycosphingolipid $G_{M1}$. This demonstrated that diverse insults such as beta-amyloid peptide (Aβ), reactive oxygen species (1 mM $H_2O_2$), NMDA, neurotrophic factor deprivation, axotomy, mitochondrial poisons (e.g., arsenite), fas ligand crosslinking, and hypoxia, induce rapid polarization of somal raft membranes. An in vitro model for neuronal death, as well as methods for its preparation and use, is provided. The in vitro model is characterized by exhibiting a novel biochemical mechanism that is utilized by many neurotoxic insults to induce death. The in vitro model finds use in a variety of applications, including screening applications for potential neurodegenerative disease and stroke therapeutic agents. In further describing the subject invention, the in vitro model will be described first followed by a discussion of representative methods for its production and a review of applications in which the in vitro models find use.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The subject invention provides a non-human animal model of neuronal death. A variety of different species of non-human animals are encompassed by the subject invention, where the subject animal neurons in the model will typically be mammalian, including non-human primates, dogs, cats, cows, pigs, and the like, where species of the order rodentia, e.g. mice, rats and guinea pigs, are of particular interest. Preferably, the subject non-human animal neurons in the model are mouse.

As the subject non-human in vitro models are ND animal models, they preferably exhibit one or more characteristics analogous to the neuronal death characteristics seen in humans suffering from ND and stroke. As such, the subject animal neuronal models exhibit condensed or fragmented chromatin.

The subject in vitro animal neurons in response to a variety of neurotoxic insults such as beta-amyloid peptide (Aβ), reactive oxygen species (1 mM $H_2O_2$), NMDA, neurotrophic factor deprivation, axotomy, mitochondrial poisons (arsenite), fas ligand crosslinking and hypoxia have polarized lipid raft microdomains. In other words, the neuronal tissue of the subject animals in response to neurotoxic agents is characterized by having established a polarization of somal membrane lipid microdomains and established a polarized signaling platform. This is as compared to a control neurons e.g. unstimulated neurons cultured from a normal animal. By polarization of lipid raft microdomains it is meant that the migration of lipid rafts and the proteins contained therein to a pole of the neuronal cell body, the soma. In this fashion, the neuronal tissue of the subject animals has established a signaling platform of lipid rafts and raft resident proteins to signal changes in the neurons environment. Generally, the neuronal cells of the brain tissue of the animal have a uniform distribution of lipid microdomains around the soma/cell body in resting neurons. Lipid raft microdomains are also distributed in signaling clusters along axons and dendrites. These clusters are reduced following exposure to neurotoxic agents. Within the lipid rafts are raft resident proteins such as glycosylphosphatidyl-inositol-anchored proteins (GPI-linked) which can be used as markers for lipid raft distribution. Lipid raft polarization is mediated by changes in the actin microtubular cytoskeleton such that actin and microtubule accumulate beneath the polarized raft complex and actin/microtubule detecting probes can also be used to mark the polarization of raft microdomains and are part of the somal polarization response. Mitochondria also re-organize beneath the polarized raft microdomains and may be used to monitor the polarization of raft microdomians and are part of the neuronal cell body response to neurotoxic stimuli. Dyes, such as the styryl dye FM1-43 may also be used to monitor neuronal raft polarization. FM1-43 is an amphipathic molecule that intercalates spontaneously into the outer leaflet of cell membranes without diffusing across the membrane. Within the lipid environment, FM1-43 exhibits 50- to 100-fold increased fluorescence intensity than the dye in aqueous solution. FM1-43 fluorescence increases in the polarized raft complex, and an increase in fluorescence can therefore be used as an index of raft polarization dynamics. Clearly, there are many ways to monitor the distribution of lipid rafts in the neuronal membrane. Probes labeled for detection which recognize sugars and gangliosides such as GM1 (cholera toxin subunit B), antibodies to proteins particular to lipid rafts (GPI-linked etc.) or lipids particular to lipid rafts, dyes which incorporate predominantly into raft domains (FM1-43) are all incorporated herein as a means to detect the distribution of raft microdomains on neuronal membranes. Many proteins are modified by fatty acid acylation with myristate or palmitate. These and such modifications help target these proteins to raft microdomains and may also be used to track the distribution of raft microdomains. The novelty of the invention disclosed herein is the polarization of neuronal soma raft microdomains as a signal transduction mechanism in response to external stimuli. The means to detect raft microdomain distribution are well known to those skilled in the art and are incorporated herein.

A critical feature of the neuronal in vitro model is that the neuronal tissue in response to neurotoxic agents is characterized by a uniform conserved biochemical mechanism which is utilized by all neurons for signal transduction. In other words, lipid raft polarization is a common biochemical mechanism utilized by all neurons as a part of their signal transduction response to toxic agent exposure. The polarization and establishment of a signaling platform in response to neurotoxin exposure is the same for all neurotoxins and is observed in the autopsy brains of human subjects suffering from neuronal death and degeneration in AD and PD. Therefore, the mechanism of neuronal death in the subject animals neuronal in vitro model is substantially similar to the lipid raft polarization mechanism observed in human AD and PD Disease subjects.

Generally, the subject animals will be embryonic animals, where by embryonic is meant an in utero animal that comprises an ability to have its neurons cultured in vitro. Typically, this neuronal culture procedure utilizes embryonic day 17 in utero pups as a source of neuronal tissue. Currently, cultured neurons are not possible from adult animals but this model would apply to such neurons if culture techniques improve.

The in vitro model is also applicable to cultured neurons from transgenic animals carrying any transgene.

In any embodiment, the transgene will be a transgene which is capable of being expressed in the brain tissue of the animal.

EXAMPLE 1

Methods for Producing the Subject In Vitro Neuronal Model

Numerous descriptions of protocols for preparing neurons are published and known to those of skill in the art. As such, methods for production of such neurons are readily practiced by those of skill in the art.

Briefly, cortical cultures enriched in cells of neuronal lineage can be prepared from 16-day mouse embryos with Neurobasal medium containing B27 supplement, 2 mM glutamate, and 1% penicillin and streptomycin. After 4 days, one-half of the medium is replaced with an appropriate medium such as Neurobasal medium containing 2% B27 growth supplement, and experiments can be conducted at 8 days in vitro a sufficient time for neurons to grow and differentiate.

The animal in vitro model neurons are then given an effective amount of a neurotoxic stimulus to induce neuronal death. The lipid raft polarization inhibitor may be any compound that inhibits or blocks the formation of the raft microdomain signaling complex. As such, the raft polarization inhibitor may be: an inhibitor of cholesterol synthesis such as HMG-CoA reductase inhibitors (statins) and the like; or an acute depleter of cholesterol, such as methyl-β-cyclodextrin (βCD).

Figure 4A:
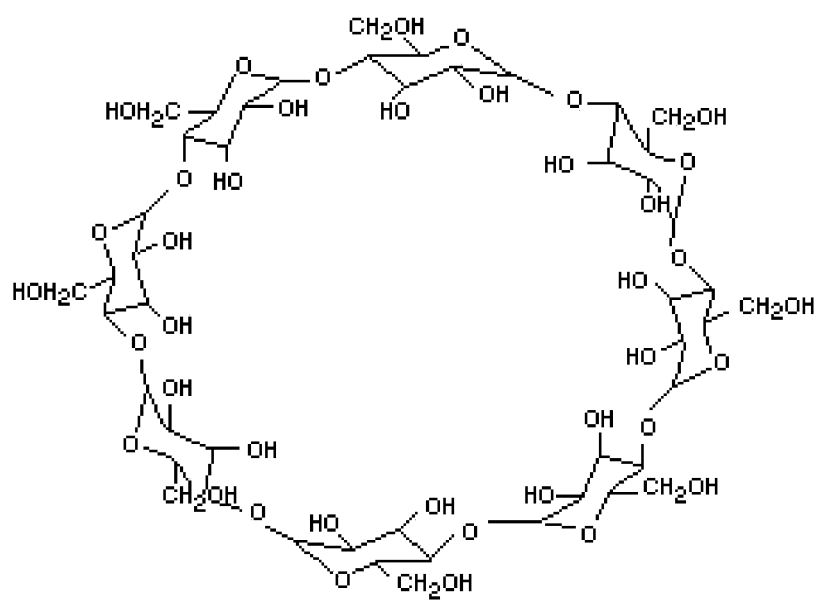
FIG. 4A is a drawing and schematic of βCD, a cholesterol depleting agent, looking down on the cavity from above.
Figure 4B:
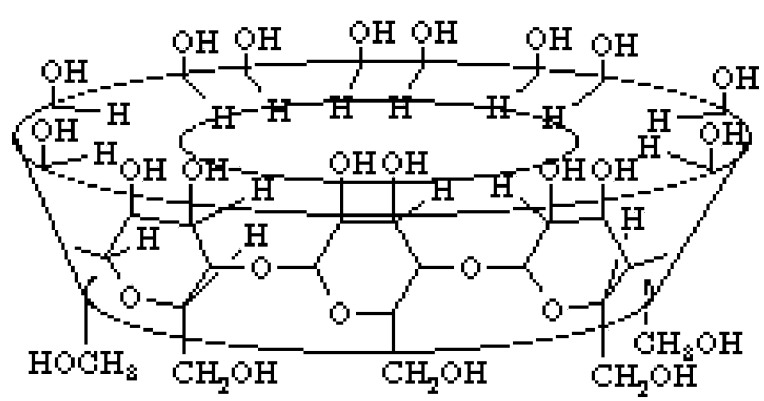
FIG. 4B presents a perspective drawing of the 3-dimensional structure of γ-cyclodextrin.
Figure 5A:
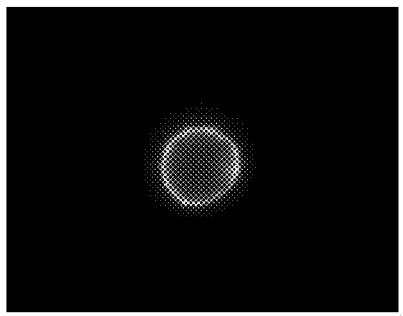
FIG. 5 shows the uniform distribution of raft microdomains around the cell bodies of neuronal precursor cells (panel A) and CD34$^+$ human stem cells (panel D). Proliferation following exposure to trophic factors induces polarization of raft microdomains in neuronal precursors (panels B and C) and stem cells (panel E). Arrows indicate polarized raft microdomains in proliferating progenitors. Cholesterol depletion inhibits raft polarization and inhibits proliferation.
Figure 5B:
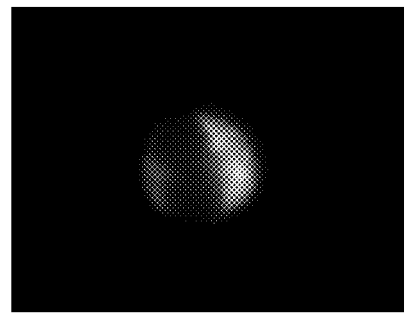
Figure 5C:
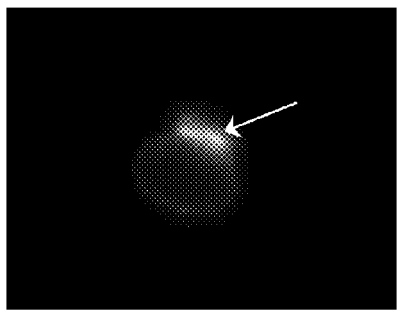
Figure 5D:
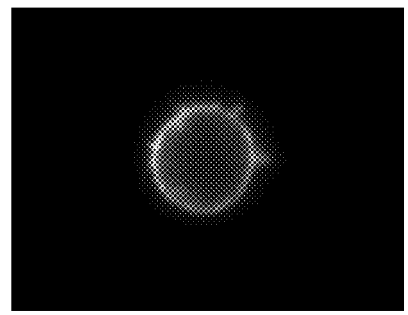
Figure 5E:
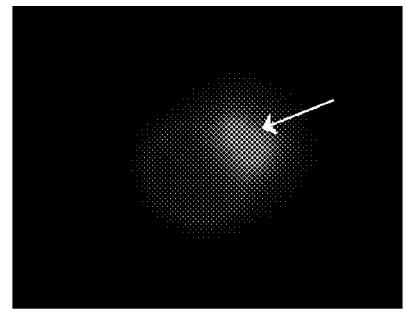

Linking D-glucose units together with α-1,4 linkages means that the growth of the polysaccharide follows a helical path (FIGS. 4A & 4B). Occasionally, this coiling brings the D-glucose at the end of the growing polymer chain close enough to the one at the beginning that a glycosidic bond can form between them, thereby creating a cyclic polysaccharide. These structures are known as cyclodextrins. FIG. 4A presents the structure of one such compound which contains a ring comprised of eight D-glucose units. This compound is known as γ-cyclodextrin. Cyclodextrins are natural products formed by the action of enzymes called cycloglucosyltransferases, CGTases, on starch. These enzymes are found in a microorganism called *Bacillus macerans*. Cyclodextrins participate in host-guest interactions, serving as hosts for a variety of small molecules. The number of monomer units in the macrocyclic ring determines the size of the cavity the host makes available to the guest.

The ability of cyclodextrins to "encapsulate" small molecules has led to their use as cholesterol depletors and disrupters of lipid rafts in cells and neurons.

In FIG. 4A, you are looking down on the cavity from above. FIG. 4B presents a perspective drawing of the 3-dimensional structure of γ-cyclodextrin. The conformation of the glucose units in the cyclodextrin places the hydrophilic hydroxyl groups at the top and bottom of the three dimensional ring and the hydrophobic glycosidic groups on the interior. Note that the polar OH groups project to the exterior of the structure while the hydrogens attached to the glucose units point into the cavity. Thus the interior is comparatively non-polar. These structural features make the polymer water soluble while still able to transport non-polar materials such as cholesterol. When cyclodextrin is applied to cells or neurons cholesterol is depleted from cellular membranes and resides within the interior non-polar cavity. The depletion of cholesterol from cell membranes disrupts lipid rafts and inhibits cell signaling through raft domains.

EXAMPLE 2

Methods of Using the Subject In Vitro Neuronal Model

The neuronal in vitro animal models exhibiting polarization of lipid microdomains find use in a variety of applications particularly in research applications, including research applications designed to elucidate the role of various genes and or agents in the development or progression of ND as well as in research applications designed to identify therapeutic agents for the treatment or amelioration of neurodegenerative disease and stroke symptoms.

For example, as the in vitro neuronal model demonstrates a biochemical mechanism analogous to those observed in human disease subjects, the model can be used to study the effect of various genes and their expression products in the development of neurodegenerative disease. Thus, the subject in vitro model is suitable for elucidation of compounds that modulate the progression of neurodegenerative disease.

Of particular interest is the use of the in vitro model for the screening of potential ND therapeutic agents. Through use of the model, one can identify compounds that modulate the progression of ND, e.g., by binding to, modulating, enhancing or repressing the activity of a protein or peptide involved in the progression of ND, e.g. a neurotoxic Aβ peptide. Screening to determine drugs that lack effect on the progression of ND is also of interest. Areas of investigation are the development of anti-degenerative or cognitive therapies. Of particular interest are screening assays for agents that have a low toxicity for human cells. Assays of the invention make it possible to identify compounds which ultimately (1) have a positive affect with respect to ND progression and as such are therapeutics, e.g. agents which arrest or reverse the neurodegeneration and or memory/learning deterioration associated with ND; or (2) have an adverse affect with respect to ND progression and as such should be avoided as therapeutic agents and in products consumed by animals, in particular humans.

A wide variety of assays may be used for this purpose, including in vivo behavioral studies, determination of the localization of drugs after administration, labeled in vitro protein-protein binding assays, protein-DNA binding assays, electrophoretic mobility shift assays, immunoassays for protein binding, and the like. Depending on the particular assay, whole animals may be used, or cells derived therefrom. Cells may be freshly isolated from an animal, or may be immortalized in culture. Cells of particular interest include neural and brain tissue of animals.

The term "agent" as used herein describes any molecule, e.g. protein or nonprotein organic pharmaceutical, with the capability of affecting the polarization of lipid microdomains underlying neuronal death. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Candidate agents for arresting and or reversing raft microdomain polarization/neuron raft remodeling, or recovery from acute insults to the nervous system can be screened for their ability to modulate ND progression. Efficacious candidates can be identified by arrest or reversal of raft microdomain polarization in comparison with untreated control neurons. In another example, a candidate agent for the treatment of impaired learning function attributable to AD can be identified by an inhibition of raft microdomain polarization following administration of the candidate agent. Alternatively, candidate agents may be identified by their ability to modulate the activity of a protein implicated in ND, and associated with raft microdomains.

Where the screening assay is a binding assay, one or more of the molecules may be joined to a label, where the label can directly or indirectly provide a detectable signal.

Various labels include radioisotopes, fluorescent or chemiluminescent moieties, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures. A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Samples, as used herein, include biological fluids such as tracheal lavage, blood, cerebrospinal fluid, tears, saliva, lymph, dialysis fluid and the like; organ or tissue culture derived fluids; and fluids extracted from physiological tissues. Also included in the term are derivatives and fractions of such fluids. The number of cells in a sample will generally be at least about $10^3$, usually at least $10^4$ more usually at least about $10^5$. The cells may be dissociated, in the case of solid tissues, or tissue sections may be analyzed.

Alternatively a lysate of the cells may be prepared. For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method depends on the in vitro detection of binding between antibodies and a protein of interest in a lysate. Measuring the concentration of binding in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples. A number of assays are known in the art for determining the effect of a drug on animal behavior and other phenomena associated with neurodegeneration or impairment of cognitive abilities as observed in AD. Some examples are provided, although it will be understood by one of skill in the art that many other assays may also be used. The subject animals may be used by themselves, or in combination with control animals.

The screen and candidate molecules identified therein using the in vitro model of the invention can employ any phenomena associated learning impairment, dementia or cognitive disorders that can be readily assessed in an animal model. The screening can include assessment of phenomena including, but not limited to: 1) analysis of molecular markers (e.g., levels of expression of particular gene product in brain tissue; presence/absence in brain tissue of particular protein isoforms; and formation of neurite plaques); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue). These phenomena may be assessed in the screening assays either singly or in any combination.

Preferably the screen will include control values (e.g., the disposition of raft microdomains in the test animal in the absence of test compound(s)). Test substances which are considered positive, i.e., likely to be beneficial in the treatment of ND are those which reverse or inhibit raft polarization in in vitro model screen.

Methods for assessing these phenomena, and the effects expected of a candidate agent for treatment of ND, are known in the art. For example, methods for using transgenic animals in various screening assays for testing compounds for an effect on ND, are found in WO 9640896, published Dec. 19, 1996.

EXAMPLE 3

Analysis of Gene Expression 1) mRNA: mRNA can be isolated by the acid guanidinium thiocyanatephenol:chloroform extraction method (Chomczvnski et al., *Anal Biochem.* 162:156-159 (1987)) from cell lines and tissues of transgenic animals to determine expression levels by Northern blots.

2) In situ Hybridizations: Radioactive or enzymatically labeled probes can be used to detect mRNA in situ. The probes are degraded approximately to 100 nucleotides in length for better penetration of cells. The procedure of Chou et al. *J Psychiatr Res.* 24:27-50 (1990) for fixed and paraffin embedded samples is briefly described below although similar procedures can be employed with samples sectioned as frozen material. Paraffin slides for in situ hybridization are dewaxed in xylene and rehydrated in a graded series of ethanols and finally rinsed in phosphate buffered saline (PBS). The sections are postfixed in fresh 4% paraformaldehyde. The slides are washed with PBS twice for 5 minutes to remove paraformaldehyde. Then the sections are permeabilized by treatment with a 20 mu g/ml proteinase K solution. The sections are refixed in 4% paraformaldehyde, and basic molecules that could give rise to background probe binding are acetylated in a 0.1M triethanolamine, 0.3M acetic anhydride solution for 10 minutes. The slides are washed in PBS, then dehydrated in a graded series of ethanols and air dried. Sections are hybridized with antisense probe, using sense probe as a control. After appropriate washing, bound radioactive probes are detected by autoradiography or enzymatically labeled probes are detected through reaction with the appropriate chromogenic substrates.

3) Western Blot Analysis: Protein fractions can be isolated from tissue homogenenates and cell lysates and subjected to Western blot analysis as described by Harlow et al., *Antibodies: A laboratory manual*, Cold Spring Harbor, N.Y., (1988); Brown et al., *J. Neurochem* 40:299-308 (1983); and Tate-Ostroff et al. *Proc Natl Acad Sci* 86:745-749 (1989)). Only a brief description is given below. The protein fractions can be denatured in Laemmli sample buffer and electrophoresed on SDS-polyacrylamide gels. The proteins are be then transferred to nitrocellulose filters by electroblotting. The filters are blocked, incubated with primary antibodies, and finally reacted with enzyme conjugated secondary antibodies. Subsequent incubation with the appropriate chromogenic substrate reveals the position of proteins.

EXAMPLE 4

Therapeutic Agents Identified with the In Vitro Model

This invention describes lipid raft polarization and establishment of a polarized raft signaling platform in neurons exposed to a variety of neuroxic insults ranging from beta-amyloid peptide (Aβ), reactive oxygen species (1 mM $H_2O_2$), NMDA, neurotrophic factor deprivation, axotomy, arsenite, fas ligand crosslinking and hypoxia. The range of neurotoxic insults is wide and is meant to indicate the diversity of neurotoxic insults which use lipid raft polarization to sense and mount a response to the insult. As such polarization of neuronal raft microdomains is an integral part of the neurons signal transduction pathway. Importantly, the raft polarization is an early part of the neurons biochemical response and as such very amenable to therapeutic intervention which would block or retard the death process.

The HMG-CoA reductase enzyme is rate limiting in cholesterol biosynthesis. Pre-treatment of cortical cultures with HMG-CoA reductase inhibitors (statins) or acute treatment with the cholesterol-extracting agent β-cyclodextrin inhibits lipid raft polarization and protects against neuronal death. This mode of depleting cholesterol to inhibit raft microdomain polarization has been used in lymphocytes to disrupt immune signaling. Neuroprotection is substantially attenuated by co-treatment with either mevalonate or cholesterol and is mimicked by acute treatment with the cholesterol-extracting agent β-cyclodextrin, indicating that neuroprotection is mediated by depletion of a cellular pool of cholesterol because of the inhibition of cholesterol biosynthesis. Mevalonate acts as a precursor of not only cholesterol but also isoprenoids for farnesyl and geranylgeranyl molecules, which have an important signaling function.

EXAMPLE 5

Cholesterol depletion inhibits lipid raft polarization and protects cortical neurons from AB peptide and NMDA-induced neuronal death as measured by LDH release and chromatin fragmentation.

Figure 3:
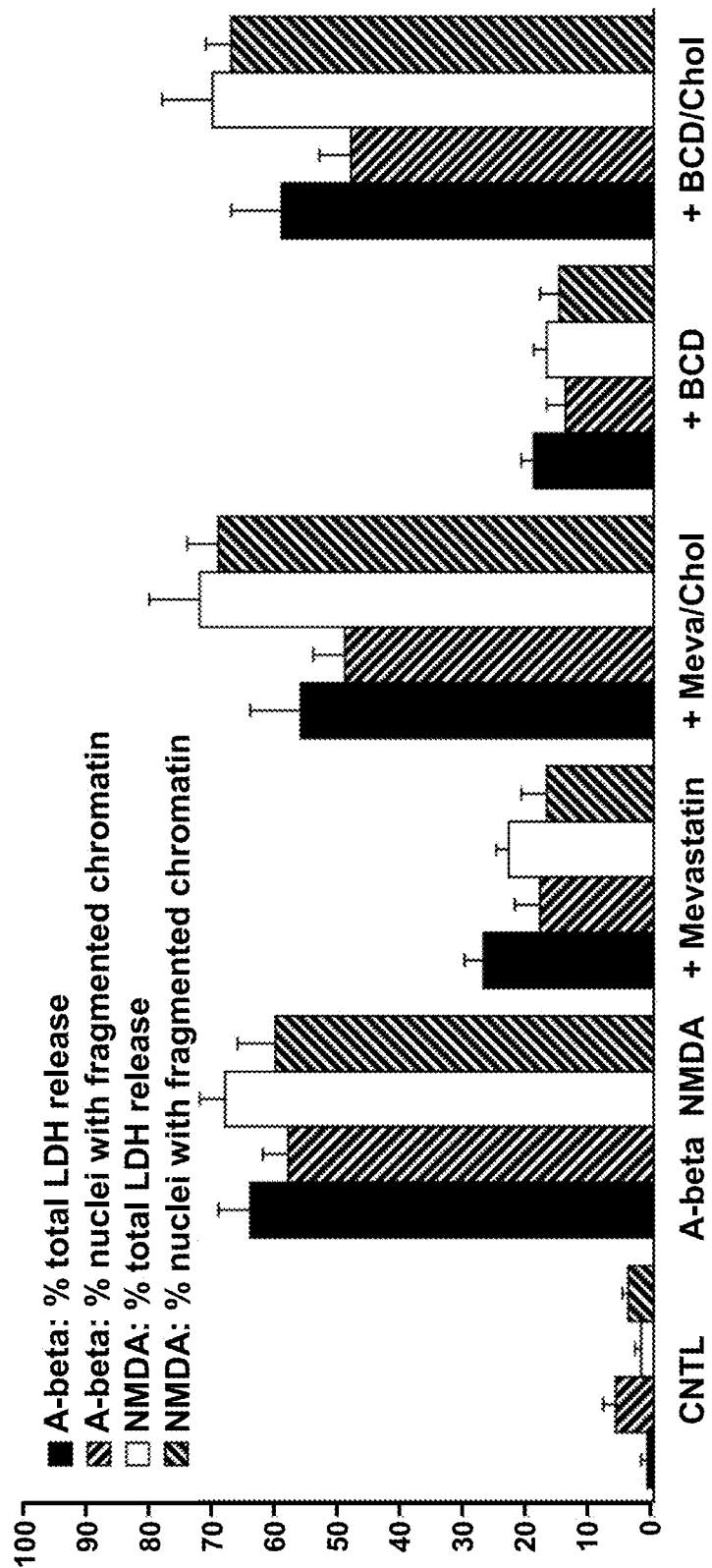
FIG. 3 shows the protective effects as assessed by LDH release assay and chromatin fragmentation of compounds which inhibit lipid raft polarization by lowering cholesterol levels in the neuronal membrane. Mevastatin, an HMG-CoA enzyme inhibitor and βCD, a cholesterol depleting agent, both inhibit lipid raft polarization and protect against neurotoxic exposure from 25 µM A-beta 25-35 peptide and 300 µM NMDA.

Cultured cortical neurons at 8 DIV were untreated (control group, CNTL), treated with 20 µM Aβ 25-35 for 48 hr (A-Beta group) or exposed to 300 µM NMDA/5 µM glycine for 10 min (NMDA group), as shown in FIG. 3. Neuronal cultures were also pre-treated chronically with 300 nM mevastatin for five days (cholesterol depleted group, $chol_{meva}$), or acutely with 1% βCD for 1 hr (cholesterol depleted group, $chol_{\beta CD}$) before 20 µM Aβ 25-35 treatment or 300 nM NMDA treatment. At the end of 48 h of 20 µM Aβ 25-35 treatment and 24 h following 300 nM NMDA exposure, culture medium was collected for LDH release assay. Cholesterol depletion induced resistance to 20 µM Aβ 25-35 or 300 nM NMDA induced neuronal death was prevented by co-incubation of 300 nM mevastatin with 5 µM cholesterol (cholesterol depleted group, $Meva_{chol}$, (A-Beta)/(NMDA)) or a 15 min treatment with 2 mM cholesterol complexed with 2.5% βCD to replace cholesterol following acute depletion with 1% βCD (cholesterol depleted group, $\beta CD_{chol}$, (Aβ)/(NMDA)). The LDH release value obtained from cortical neurons exposed to 1% Triton X-100-containing lysis buffer served as 100% LDH release, and data obtained in other groups were calculated as percent of this value accordingly. Data are expressed as the mean ±S.E.M (n=3). Control and cholesterol depleted cortical neurons were assessed for chromatin integrity (DAPI) and CTx-B staining distribution following 20 µM Aβ 25-35 and 300 nM NMDA treatment. We determined the percentage of neurons with polarized CTx-B staining and the percent nuclei with condensed and fragmented chromatin for each experimental group of neurons by counting 500 neurons in several random fields. Three hours following 20 µM Aβ 25-35 or 1 h following 300 µM NMDA treatment, the percentage of neurons with polarized raft microdomains is significantly lower and 48 h following 20 µM Aβ 25-35 or 24 h following 300 µM NMDA treatment the percentage of neurons with condensed and fragmented chromatin is significantly lower in cholesterol-depleted neurons.

The 3-hydroxy-3-methyl-glutaryl-coenzyme A (HMG-CoA) reductase inhibitors (statins) reduce synthesis of cholesterol and isoprenoids, molecules that modulate diverse cell function. Inhibition of the enzyme HMG-CoA reductase depletes downstream isoprenoids such as geranylgeranyl pyrophosphate and farnesyl pyrophosphate. These isoprenoids not only serve as intermediates for cholesterol biosynthesis but modify proteins to facilitate their attachment to cell membranes. For example, HMG-CoA inhibition blocks geranylgeranylation of G-proteins such as Rho GTPases, thereby inhibiting GTPase activity and causing disruption of actin stress fibers. Thus, raft microdomain polarization and neuronal death is blocked by cholesterol depletion, rho GTPase inhibition, or inhibition of geranyl and farnesyl membrane attachment moieties. These different modes of raft polarization are targets for therapeutic intervention.

All statins inhibit polarization of lipid microdomains in vitro and are protective against neurotoxic insults. However, all statins may not be equipotent in protecting the brain against neurotoxic insults in vivo. The differences between statins may relate to variable drug penetration into the brain based on differences in lipophilicity. For example, the active form of mevastatin is approximately 8 times less lipophilic than simvastatin, and lovastatin is less lipophilic than simvastatin. Hence, statins with the highest lipophilicity and potency may provide the greatest degree of neuro-protection.

Filipin is a polyene antibiotic that specifically complexes cholesterol and disrupts lipid raft function.

Rho kinase inhibitor Y-27632.

Pre-treatment of cortical cultures with cytochalasin D, a drug that prevents actin polymerization, prevents the polarization of lipid microdomains.

Pre-treatment of cortical cultures with cytochalasin D or latrunculins, drugs that prevents actin polymerization, prevents the polarization of lipid microdomains.

The HMG-CoA reductase enzyme is rate limiting in cholesterol biosynthesis. HMG-CoA reductase inhibitors protect cortical neurons from NMDA mediated excitotoxicity and reduce infarct volume after cerebral ischemia in mice. Pre-treatment of cortical cultures with HMG-CoA reductase inhibitors (statins) or acute treatment with the cholesterol-extracting agent β-cyclodextrin inhibits lipid raft polarization and protects against neuronal death. Neuroprotection is substantially attenuated by co-treatment with either mevalonate or cholesterol and is mimicked by acute treatment with the cholesterol-extracting agent β-cyclodextrin, suggesting that neuroprotection is mediated by depletion of a cellular pool of cholesterol because of the inhibition of cholesterol biosynthesis.

Polyunsaturated fatty acids (PUFA) n-3 inhibit raft microdomain polarization. PUFA n-3 are more effective than PUFA n-6 in inhibiting raft polarization following neurotoxic exposure.

n-Butyrate, carnitine and related compounds also inhibit raft polarization.

Selected analogues of propranolol (alprenolol, oxprenolol, metoprolol, practolol, and sotalol) calmodulin inhibitors phenothiazine-drugs whose activities can be differentiated as follows: trifluoperazine greater than chlorpromazine greater than sulfoxide derivatives immunosuppressants FK-506 rapamycin cyclosporine Ether-linked lysophospholipids and alkylphosphocholines anti-tumor ether lipids ET-18-OCH$_3$ and hexadecylphosphocholine Erythropoietin Inhibitors of mek (map/erk) kinases Neuronal cultures derived from embryonic precursors contain neuronal precursors which in response to trophic factors divide and differentiate into neurons. Similar proliferative events occur in in vitro human stem cell division whereby stem cells divide before entering terminal differentiation. The process of proliferation before final differentiation also utilizes specific signal transduction mechanisms. These proliferative events in neuronal progenitor cells and human stem cells both utilize polarization of raft microdomains to organize signaling elements at a specific pole of the cell body. Similar conservation of cytoarchitectual form is seen in the immune system whereby lymphocytes use a polarized cap structure to signal both proliferation and death. As such, the formation of this signaling complex for proliferation of neuronal progenitors and stem cells is also sensitive to cholesterol depleting drugs and drugs which impair the formation of the death inducing raft microdomain. Drugs which impair formation of raft polarization could enhance terminal differentiation.

The in vitro model can be used to identify additional therapeutic agents for the treatment and/or amelioration of neuronal death, e.g. for use in slowing or reversing neurodegeneration and/or the degeneration of learning/memory abilities. By treatment is meant at least a reduction in an neurodegenerative disease or stroke parameter. such as a slowing in the progression of the disease, a reduction in the magnitude of a symptom thereof, e.g. a reduction in the level of learning impairment. and the like.

With neurodegenerative disease and stroke/trauma patients, the therapeutic agents identified using the subject animal models may be administered in a variety of ways, such as orally. topically. parenterally e.g. subcutaneously. intraperitoneally, by viral infection. intravascularly. etc. Inhaled treatments are of particular interest. Depending upon the manner of introduction, the compounds may be formulated in a variety of ways. The concentration of therapeutically active compound in the formulation may vary from about 0.1-100 wt. %.

The pharmaceutical compositions can be prepared in various forms. such as granules, tablets, pills, suppositories, capsules, suspensions. salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The foregoing examples are offered by way of illustration and not by way of limitation. It is apparent from the above results and discussion that the identification of a novel neuronal biochemical mechanism is provided by the subject invention. In this model, neurons exposed to neurotoxic stimuli are characterized by the polarization of raft microdomains analogous to that observed in human ND patients, providing for an animal model that more closely correlates to human disease and injury as compared to other currently known neuronal models.

As such, the subject invention provides for a significant advance in the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A population of cholesterol-depleted mammalian stem cells in vitro, produced by the process comprising:
   (a) culturing a starting population comprising mammalian stem cells in a cell culture medium;
   (b) amplifying and/or enriching for said cholesterol-depleted mammalian stem cells by adding 1% cyclodextrin to the cell culture medium in which said starting population is cultured.

2. The population of cholesterol-depleted mammalian stem cells of claim 1, wherein the cyclodextrin is methyl-β-cyclodextrin.

3. The population of cholesterol-depleted mammalian stem cells of claim 2, wherein said stem cells are resistant to insult as measured by a method from the group consisting of LDH release assay and chromatin fragmentation.

4. The population of cholesterol-depleted mammalian stem cells in vitro of claim 1, wherein said starting population remains in contact with said cell culture medium comprising 1% cyclodextrin for about 1 hour to about 49 hours.

5. A population of mammalian stem cells having inhibited lipid raft polarization in vitro, produced by the process comprising:
   (a) culturing a starting population comprising mammalian stem cells in a cell culture medium;
   (b) amplifying and/or enriching for said mammalian stem cells having inhibited lipid raft polarization by adding 1% cyclodextrin to the cell culture medium in which said starting population is cultured.

6. The population of mammalian stem cells having inhibited lipid raft polarization of claim 5, wherein the cyclodextrin is methyl-β-cyclodextrin.

7. The population of mammalian stem cells having inhibited lipid raft polarization in vitro of claim 5, wherein said starting population remains in contact with said cell culture medium comprising 1% cyclodextrin for about 1 hour to about 49 hours.

8. A population of cholesterol-depleted mammalian stem cells in vitro, produced by the process comprising:
   (a) culturing a starting population comprising mammalian stem cells in a cell culture medium;
   (b) amplifying and/or enriching for said cholesterol-depleted mammalian stem cells by adding at least about 0.1% methyl-β-cyclodextrin to the cell culture medium in which said starting population is cultured.

9. The population of cholesterol-depleted mammalian stem cells in vitro of claim 8, wherein said methyl-β-cyclodextrin is 1% methyl-β-cyclodextrin.

10. The population of cholesterol-depleted mammalian stem cells in vitro of claim 8, wherein said starting population remains in contact with said cell culture medium comprising methyl-β-cyclodextrin for about 1 hour to about 49 hours.

11. The population of cholesterol-depleted mammalian stem cells in vitro of claim 10, wherein said methyl-β-cyclodextrin is 1% methyl-β-cyclodextrin.

12. A method of producing a population of cholesterol-depleted mammalian stem cells, the method comprising administering 1% cyclodextrin to the growth medium in which a starting population comprising mammalian cells in vitro is cultured.

13. The method of claim 12, wherein the cyclodextrin is methyl-β-cyclodextrin.

* * * * *